(12) United States Patent
Otto et al.

(10) Patent No.: US 8,287,589 B2
(45) Date of Patent: Oct. 16, 2012

(54) REMOVAL OF TUBULAR TISSUE SUPPORTS

(75) Inventors: Veit Otto, St. Wendel (DE); Ali Abdullah Tareq Hasson, Aachen (DE); Dagmar Boltersdorf, Kreuzau (DE)

(73) Assignee: Helmholtz-Zentrum Geesthacht Zentrum Fuer Material- Und Kuestenforschung GmbH, Geesthacht (DE)

( * ) Notice: Subject to any disclaimer, the term of this patent is extended or adjusted under 35 U.S.C. 154(b) by 0 days.

(21) Appl. No.: 12/095,271

(22) PCT Filed: Nov. 27, 2006

(86) PCT No.: PCT/IB2006/004247
§ 371 (c)(1),
(2), (4) Date: Oct. 17, 2008

(87) PCT Pub. No.: WO2007/132294
PCT Pub. Date: Nov. 22, 2007

(65) Prior Publication Data
US 2009/0306677 A1    Dec. 10, 2009

(30) Foreign Application Priority Data

Nov. 28, 2005 (DE) .......................... 10 2005 056 532

(51) Int. Cl.
*A61F 2/06* (2006.01)

(52) U.S. Cl. ........................ 623/1.19; 623/1.11; 128/898
(58) Field of Classification Search ................. 606/108, 606/191; 623/1.11; 604/291
See application file for complete search history.

(56) References Cited

U.S. PATENT DOCUMENTS

| 5,197,978 A | 3/1993 | Hess |
| 5,716,410 A * | 2/1998 | Wang et al. .................. 623/1.22 |
| 6,388,043 B1 * | 5/2002 | Langer et al. .................... 528/80 |
| 7,524,329 B2 * | 4/2009 | Rucker ........................ 623/1.12 |
| 2005/0216074 A1 * | 9/2005 | Sahatjian et al. ............. 623/1.11 |

FOREIGN PATENT DOCUMENTS

| DE | 103 57 744 A1 | 1/2005 |
| DE | 103 57 742 A1 | 3/2005 |
| WO | 2004/032799 A | 4/2004 |

OTHER PUBLICATIONS

Int'l Search Report received in corresponding International Application No. PCT/IB2006/004247.

* cited by examiner

*Primary Examiner* — Kathleen Sonnett
*Assistant Examiner* — Sarah Webb
(74) *Attorney, Agent, or Firm* — Sughrue Mion, PLLC

(57) ABSTRACT

The invention provides a process by which tubular tissue supports (stents) can be removed from hollow organs of humans or of animals after heating to a temperature below the transition temperature Ttrans until softening occurs.

18 Claims, No Drawings

REMOVAL OF TUBULAR TISSUE SUPPORTS

CROSS REFERENCE TO RELATED APPLICATIONS

This application claims priority under 35 U.S.C. §371 to International Application No. PCT/IB2006/004247 (filed Nov. 27, 2006) which claims priority to German Application No. DE 10 2005 056 532.8 (filed Nov. 28, 2005), each of which applications are expressly incorporated herein by reference in their entirety.

BACKGROUND OF THE INVENTION

1. Field of the Invention

The invention relates to removal of tubular tissue supports (stents) from hollow organs of humans and/or animals.

2. Description of the Related Art

A stent (medical technology) is an implant which is introduced into hollow organs (e.g. into veins or arteries, bile ducts, the trachea or the esophagus) in order to brace the wall radially outwards. Examples of use of stents are in coronary vessels for prophylaxis of restenosis after PTCA (percutaneous transluminal coronary angioplasty).

Stents are small grid structures in the form of a tube composed of metal or of polymers, often used in the context of angioplasty, in which strictures in vessels are widened. In cancer treatment, stents serve to prevent closure of strictures caused by malignant tumors in respiratory passages, bile ducts or the esophagus, after these have been expanded.

Stents are usually cylindrical products composed of a type of wire mesh (wire coil design) or of tubes, which may be perforated or unperforated (slotted tube design). The length of commonly used stents is from 1 to 12 cm, their diameter being from 1 to 12 mm.

A stent is subject to various requirements. First, the support has to exert large radial forces on the hollow organ requiring support. Second, the support must be able to be compressed radially to permit its easy introduction into a hollow organ without at the same time injuring the vessel wall or the surrounding tissue.

In order to meet the above requirements, the stents are used in compressed form and not expanded until the correct location has been reached. In the compressed condition, the diameter is markedly smaller than in the expanded condition. In principle, this procedure can also be utilized for minimally invasive removal of the stent. However, one possible problem here is that the metallic materials usually used are riot always capable of entirely uniform expansion and recompression, and there is a resultant potential risk of injury to adjacent tissue.

Two different technologies are used for minimally invasive stent use: (1) expandable-balloon stents (system composed of balloon, catheter, stent); and (2) self-expandable stents (system composed of introductory sheath (protective sheath), catheter, stent).

Self-expanding stents are generally composed of shape-memory materials (SM material). Shape-memory materials are materials which change their external shape on exposure to an external stimulus. The materials are, by way of example, capable of controlled change in their shape when the temperature is increased above what is known as the switching temperature ($T_{trans}$). The shape-memory effect is utilized for "spontaneous" enlargement of the diameter of the stent, and to fix the stent at the location of use.

The shape-memory effect is not a specific property of any of the materials. Rather, it is a direct result of the combination of structure and morphology and of a processing/programming technology.

In shape-memory materials, a distinction is made between a permanent and a temporary shape. The material is first converted to its permanent shape, using conventional processing methods (e.g., extrusion). The material is then converted, reshaped and fixed into its desired temporary shape. This procedure is also termed programming. It is composed either of heating of the specimen, reshaping and a cooling procedure, or else of the shaping at relatively low temperature. The permanent shape has been held in memory, while the temporary shape is actually present Heating of the material to a temperature higher than the transition temperature for a change of morphology (switching temperature) triggers the shape-memory effect and thus causes resumption of the permanent shape held in memory.

The shape-memory effect, which permits controlled alteration in the shape of a material by application of an external stimulus is described, by way of example, in the overview articles "Shape Memory Alloys", *Scientific American*, vol. 281, 74-82 (1979) and *Angew. Chem.*, 114, 2138-2162 (2002).

An example of a metallic SM material used is nitinol, an equiatomic alloy composed of nickel and titanium (*J. Appl. Phys.*, 34, 1475 (1963)). However, nitinol cannot be used when nickel allergy is present. The material is moreover very expensive and programmable only by complex methods. This programming process needs comparatively high temperatures, and programming in the body is therefore impossible. The SM material is therefore programmed outside the body, (i.e. converted to its temporary shape). After implantation, the shape-memory effect is then triggered and the stent is expanded, i.e. regains its permanent shape. Removal of the stent by again utilizing the shape-memory effect is then impossible. Another frequent problem with metallic stents, not only in the vascular sector, is occurrence of restenosis.

In contrast, other metallic stents composed of SM materials, for example those described in U.S. Pat. No. 5,197,978, also permit utilization of the shape-memory effect for stent removal. However, production of these metallic materials is very complicated and tissue compatibility is not always ensured. Inflammation and pain patterns occur because of the poor matching of the mechanical properties of the stent.

The temporary stent described in U.S. Pat. No. 5,716,410 is a spiral composed of a polymeric shape-memory material (SMP). The SMP material includes an embedded heating wire. The heating wire has connection by way of a catheter shaft to an electrical control unit, the end of the shaft taking the form of a hollow tube pushed over one end of the spiral. If the implanted stent in its expanded, temporary shape is heated above the switching temperature $T_{trans}$, the diameter of the spiral decreases. The intention is that this permits easy removal of the stent. A disadvantage of the spiral structure is that the radial forces are too small to expand tubular cavities. The radial forces of the spiral are distributed merely over a very small area of contact with the tissue; there is the danger of local mechanical pressure-overloading, and indeed in some instances incision into the tissue. Furthermore, it is difficult to secure the catheter shaft (heating element) to the heating wire of the implanted spiral because first the catheter shaft has to be pushed over one end of the spiral.

U.S. Pat. No. 5,964,744 describes implants, such as tubes and catheters, for the urogenital sector or gastro-intestinal tract composed of polymeric shape-memory materials which comprise a hydrophilic polymer. In an aqueous medium the material absorbs moisture and thus softens and changes its shape. The material can also soften on heating. In the case of the ureteral stent, the effect is utilized in order to flex the straight ends of the stent at the location of use (e.g. kidneys and bladder). The result is to fix the ureteral stent at the location of use, so that the stent cannot slip during peristaltic movements of the tissue.

WO 02141929 describes tubular vessel implants with shape memory which are also suitable, by way of example as bile duct stents. The material is an aliphatic, polycarbonate-based thermoplastic polyurethane with biostability.

The shape memory polymer stents known from DE 10357747 and DE 10357744 do not need to be removed from the body because of their biodegradability. The materials for the stents are described therein to be elastic only when heated above the transition temperature $T_{trans}$ of the polymer.

DE 10357743 and DE 10357742 describe temporary shape memory polymer stents, that are heated above the transition temperature $T_{trans}$ of the polymer to change their shape to a smaller form before their removal.

U.S. Pat. No. 6,245,103 describes bioabsorbable, self-expanding stents composed of braided filaments. Here, a stent is compressed by applying an external radial force. The stent has been mounted on a catheter and is held in stressed, compressed condition by an outer sheath. When the stent is expelled from this arrangement its diameter spontaneously enlarges because of the resilience of the elastic material. This change is not the shape-memory effect, which is triggered by an external stimulus, (e.g., a temperature increase.

Removal of an expanded stent, as indicated above, is difficult. When the stent has to be withdrawn from a tubular cavity there is a risk that the surrounding tissue will be injured by abrasion in the process, because the stent is too large and has sharp edges. The shape-memory effect is, therefore, also used again to reduce the diameter of the stent when the stent is in turn to be removed. Examples of removable stents composed of metals with shape-memory properties are known (See, e.g., U.S. Pat. Nos. 6,413,273; 6,348,067; 5,037,427 and 5,197,978.

SUMMARY OF THE INVENTION

When the stent is removed from the hollow organ it is desirable that the diameter of the stent is substantially retained. The intention is that it should also be possible here to make use of polymers which have no, or only weak, shape-memory properties. The thermal stress to which the relevant organ is exposed should be minimal.

An object of the invention is therefore to provide a process for removal of stents from a hollow organ in which the diameter (the cross section) of the stent and its three dimensional form is substantially retained over its complete length, to not hinder the flow of body fluid.

Further objects of the invention are stents usable in the process of the invention and polymers usable for the manufacture of such stents.

A process for removal of tubular tissue supports (stents) from hollow organs of humans or of animals has been invented, and is characterized in that the implanted tissue support is heated to a temperature below the transition temperature $T_{trans}$ until softening occurs and then undergoes minimally invasive withdrawal from the hollow organ. The transition temperature can be a glass transition temperature of amorphous regions or a melting point of crystalline regions. The general term $T_{trans}$ is used below for this temperature.

According to the inventive process, the diameter of the stent is substantially retained, and therefore also is the flow of body fluid. The organ is subjected to very little thermal stress, because only very slight heating of the stent is sufficient for softening to occur. It has been found, that by heating the stent close below $T_{trans}$, it is soft enough not to harm the body on removal. On the other hand, contrary to the situation at or above $T_{trans}$, the stent is stable enough to maintain its shape and will not collapse or crumple and thereby the flow of body fluid will not be blocked during removal of the stent. This behavior is particularly advantageous for the removal of stents from vessels, where the continuous flow of body fluids is critical. This is by way of example generally the case for blood vessels and particularly important for coronary and cerebral blood vessels.

For the purposes of the invention, stents are generally composed of one or more polymeric hydrocarbons, particularly of elastomers. By way of example, suitable polymers can be used from the urethanes, polyethers, polyesters, polycarbonates, and polyamides series.

Preferably, the polymers have shape-memory properties (SMP materials), as for such materials usually the best compromise between softness and conformational stability can be effected.

For the purposes of the invention, the polymers can for example be thermoplastics, blends and networks, networks being particularly preferred. Composites composed of biodegradable SMP with inorganic, degradable nanoparticles are also suitable.

For the purposes of the invention, stents are intended to be composed in essence of the polymer, and can be biodegradable. The use envisaged for the stent here determines its form, for example type of surface (microstructuring) or the presence of coatings, etc.

DETAILED DESCRIPTION OF THE PREFERRED EMBODIMENTS

The surface of the stent has been formed so as to be compatible with the physiological environment at the location of use, via suitable coating (e.g., hydrogel coating) or surface microstructuring. Parameters such as pH and the number of microbes present have to be considered as a function of the location of use during design of the stent.

Endothelial cells are then used to colonize the surface, and this can be promoted, if appropriate, by suitably modifying the surface (e.g., coating). The result is that growth of endothelial cells gradually covers the stent.

In another alternative, the stent is intended to remain outside the endothelial layer after fitting, and this can be achieved by suitable measures, such as selection of the surface, segment selection for the polymeric materials, etc.

Suitable materials for the stents of the invention are described below.

SMP materials which can be used for the purposes of the invention are capable by virtue of their chemical and physical structure of carrying out controlled changes of shape. The materials can have, besides their actual permanent shape, another shape which can be impressed temporarily on the material. These materials are characterized by two structural features: crosslinking points (physical or covalent) and switching segments.

SMPs with a thermally induced shape-memory effect have at least one switching segment with a transition temperature in the form of a switching temperature. The switching segments form temporary crosslinking sites which separate on heating above the transition temperature and form again on cooling. As described above for the general case, the transition temperature can be a glass transition temperature of amorphous regions or a melting point of crystalline regions. The general term $T_{trans}$ is used below for this temperature.

Above $T_{trans}$, the material is in the amorphous condition and is very elastic and deformable. If, therefore, a specimen is heated above the transition temperature $T_{trans}$, then deformed in the flexible condition, and cooled again below the transition temperature, the chain segments are fixed in the deformed condition by virtue of freezing of degrees of freedom (programming). Temporary crosslinking sites (non-covalent) are formed, making it impossible for the specimen to revert to its original shape, irrespective of whether any external load is applied. On reheating to a temperature above the transition temperature, these temporary crosslinking sites are again separated and the specimen reverts to its original shape. The temporary shape can be produced again by renewed programming. The precision with which the original shape is regained is termed the recovery ratio.

In photo-switchable SMPs, the function of the switching segment is assumed by photoreactive groups which can be linked to one another reversibly by irradiation with light. In this case, the programming of a temporary shape and regeneration of the permanent shape takes place by virtue of irradiation with no need for any temperature change.

In principle, all SMP materials can be used to produce stents. By way of example, reference may be made here to the materials and the production processes described in: DE 10208211 A1, DE 10215858 A1, DE 10217351 A1, DE 10217350 A1, DE 10228120 A1, DE 10253391 A1, DE 10300271 A1, DE 10316573 A1 and EP 99934294 A1 and EP 99908402 A1.

SMP materials with two or more temporary shapes have been disclosed in U.S. Pat. No. 6,388,043, the disclosure of which is incorporated herein by reference in its entirety. When using SMP materials with at least one permanent and two temporary shapes for the present invention, one of the temporary shapes can correspond to a radially expandable shape usable for deployment of the stent and a second temporary shape to the expanded shape after implantation into the vessel. A further temporary shape or the permanent shape can than be triggered if needed to further expand the stent or to decrease its diameter again. A further expansion can be helpful, if the vessel has a greater inner diameter than was diagnosed or after a restenosis. A triggered contraction can also be useful to better fit the stent to the vessel or as a separate step before the removal of the stent according to the present invention, that is done below the transition temperature. If the stent has more than two temporary forms, expansion as well as contraction can both be triggered at a given time or can be triggered stepwise. When using SMP materials with two or more temporary shapes, preferably the removal of the stent according to the invention is done at temperatures below the lowest $T_{trans}$ related to any of said shapes.

Thermoplastic elastomers can preferably be used to produce the inventive stents. Suitable thermoplastic elastomers feature at least two transition temperatures. The higher transition temperature can be attributed to the physical crosslinking points which determine the permanent shape of the stent. The lower transition temperature at which the shape-memory effect can be triggered can be attributed to the switching segments (switching temperature, $T_{trans}$). The switching temperature of suitable thermoplastic elastomers is typically approximately 3 to approximately 20° C. above body temperature.

Examples of thermoplastic elastomers are multiblock copolymers. Preferred multiblock copolymers are composed of blocks (macrodiols) composed of α,ω-diol polymers of poly(ε-caprolactone) (PCL), poly(ethylene glycol) (PEG), poly(pentadecalactone), poly(ethylene oxide), poly(propylene oxide), poly(propylene glycol), poly(tetrahydrofuran), poly(dioxanone), poly(lactide), poly(glycolide) and poly(lactide-ran-glycolide) or of α,ω-diol copolymers of the monomers on which the abovementioned compounds are based, in a range of molecular weight $M_n$ of from approximately 250 to approximately 500,000 g/mol. Two different macrodiols are linked with the aid of a suitable bifunctional coupling reagent (specifically an aliphatic or aromatic diisocyanate or diacyl chloride or phosgene) to give a thermoplastic elastomer with molecular weights $M_n$ in the range from approximately 500 to approximately 50,000,000 g/mol. In a phase-segregated polymer, a phase with at least one thermal transition (glass transition or melt transition) can be allocated in each of the blocks of the abovementioned polymer, independently of the other block.

Particular preference is given to multiblock copolymers composed of macrodiols based on pentadecalactone (PDL) and ε-caprolactone (PCL) and a diisocyanate. The switching temperature—in this case a melting point—can be adjusted by way of the block length of the PCL in the range from about approximately 30 to approximately 55° C. The physical crosslinking points for fixing of the permanent shape of the stent are formed by a second crystalline phase whose melting point is in the range from approximately 87 to approximately 95° C. Blends composed of multiblock copolymers are also suitable. Controlled adjustment of the transition temperatures is possible via the mixing ratio.

It is a preferred embodiment of the invention to use polymer networks including interpenetrating networks (IPN's) to produce the inventive stents. Suitable polymer networks feature covalent crosslinking points and at least one switching segment with at least one transition temperature. The covalent crosslinking points determine the permanent shape of the stent. Suitable IPN's are obtainable by crosslinking of monomers or prepolymers in the presence of a thermoplastic polymer.

It has also been found that polymer networks are particularly suitable to incorporate additives like radioactive markers or magnetic particles therein, because the forces exhibited by the shape memory effect and the mechanical stability of the expanded form are only weakened to a minor extend when using polymer networks in combination with such additives. In an embodiment of the invention, the stent comprises up to approximately 25 weight-%, preferably about approximately 1 to approximately 20 weight-% and particularly preferred approximately 5 to approximately 15 weight-% additives like radioactive markers, or pigments like magnetic particles. The additives are used in an amount as low as possible, that is sufficient for the function of the additive, (e.g., for detectability in case of the markers). If magnetic particles are incorporated in the stent of the invention, they are used in an amount to sufficiently heat the stent inductively. As described above, it is preferred that the stent of the invention comprises network polymers, if additives in an amount specified above are incorporated therein.

To produce a covalent polymer network, one of the macrodiols described in the above section is crosslinked with the aid of a multifunctional coupling reagent. This coupling reagent can be an at least trifunctional, low-molecular-weight compound, or a polyfunctional polymer. If it is a polymer it can be a star polymer with at least three arms, a graft polymer having at least two side chains, a hyperbranched polymer, or a dendritic structure. In the case of the low-molecular-weight, and also the polymeric, compounds the end groups have to be capable of reaction with the diols. Specifically, isocyanate groups can be used for this purpose (polyurethane networks).

Particular preference is given to amorphous polyurethane networks composed of triols and/or tetrols and diisocyanate. Star-shaped prepolymers, such as oligo[(rac-lactate)-co-glycolate]triol or -tetrol are prepared via ring-opening copolymerization of rac-dilactide and diglycolide in the melt of the monomers using hydroxy-functional initiators, with addition of dibutyltin(IV) oxide (DBTO) as catalyst. Initiators used for the ring-opening polymerization reaction are ethylene glycol, 1,1,1-tris(hydroxymethyl)ethane and pentaerythritol. Oligo(lactate-co-hydroxycaproate)tetrols and oligo(lactatehydroxy-ethoxyacetate)tetrols and [oligo(propylene glycol)-block-oligo(rac-lactate)-co-glycolate)]triols are produced analogously. The inventive networks can be obtained simply via reaction of the prepolymers with diisocyanate, e.g. with an isomer mixture composed of 2,2,4- and 2,4,4-trimethylhexane 1,6-diisocyanate (TMDI), in solution e.g. in dichloromethane, and subsequent drying.

The macrodiols described in the above section can moreover be functionalized to give corresponding α,ω-divinyl compounds, which can be crosslinked thermally or photochemically. The functionalization preferably permits covalent linkage of the macromonomers via reactions which give no by-products. This functionalization is preferably rendered available via ethylenically unsaturated units, particularly preferably via acrylate groups and methacrylate groups, particular preference being given to the latter. Specifically, the reaction here to give α,ω-macrodimethacrylates or macrodiacrylates can be carried out via the reaction with the corresponding acyl chlorides in the presence of a suitable base. The networks are obtained via crosslinking of the end-group-functionalized macromonomers. This crosslinking can be achieved by irradiation of the melt, comprising the end-group-functionalized macromonomer component and, if appropriate, a low-molecular-weight comonomer as explained below. Suitable process conditions for this are irradiation of the mixture in the melt, preferably at temperatures in the range from approximately 40 to approximately 100° C., with light whose wavelength is preferably from approximately 30 to approximately 500 nm. An alternative possibility is thermal crosslinking, if a corresponding initiator system is used.

If the macromonomers described above are crosslinked, the products are networks with a uniform structure if only one type of macromonomer is used. If two types of monomer are used, AB-type networks are obtained. These AB-type networks can also be obtained if the functionalized macromonomers are copolymerized with suitable low-molecular-weight or oligomeric compounds. If the macromonomers have been functionalized with acrylate groups or with methacrylate groups, suitable compounds which can be copolymerized are low-molecular-weight acrylates, methacrylates, diacrylates or dimethacrylates. Preferred compounds of this type are acrylates such as butyl acrylate or hexyl acrylate, and methacrylates such as methyl methacrylate and hydroxyethyl methacrylate.

The amount present of these compounds which can be copolymerized with the macromonomers, based on the network composed of macromonomer and of the low-molecular-weight compound, can be from approximately 5 to approximately 70% by weight, preferably from approximately 15 to approximately 60% by weight. Incorporation of varying amounts of the low-molecular-weight compound takes place via addition of corresponding amounts of compound to the mixture requiring crosslinking. The amount of the low-molecular-weight compound incorporated into the network corresponds to the amount present in the crosslinking mixture.

The macromonomers to be used according to the invention are described in detail below.

Networks with varying crosslinking densities (or segment lengths) and mechanical properties can be achieved by varying the molecular weight of the macrodiols. The number-average molecular weight of the macromonomers requiring covalent crosslinking, determined via GPC analysis, is preferably from approximately 2,000 to approximately 30,000 g/mol, preferably from approximately 5,000 to approximately 20,000 g/mol and particularly preferably from approximately 7,500 to approximately 15,000 g/mol. The macromonomers requiring covalent crosslinking preferably have a methacrylate group at both ends of the macromonomer chain. This type of functionalization permits crosslinking of the macromonomers by simple photoinitiation (irradiation).

The macromonomers are preferably polyester macromonomers, particularly preferably polyester macromonomers based on ε-caprolactone. Other possible polyester macromonomers are based on lactide units, glycolide units, p-dioxanone units and mixtures of these and mixtures with ε-caprolactone units, particular preference being given here to polyester macromonomers having caprolactone units. Other preferred polyester macromonomers are poly(caprolactone-co-glycolide) and poly(caprolactone-co-lactide). The transition temperature can be adjusted by way of the quantitative proportion of the comonomers, as also can the degradation rate.

The macromonomers to be used according to the invention are particularly preferably macrodimethacrylates, that include the crosslinkable end groups. A particularly preferred polyester to be used according to the invention is a polyester based on ε-caprolactone or pentadecalactone, for which the statements made above concerning molecular weight are applicable. This type of polyester macromonomer, functionalized at the ends, preferably with methacrylate groups, can be prepared via simple syntheses known per se. These networks, ignoring the other substantive polymeric component of the present invention, exhibit semicrystalline properties, and their melting point of the polyester component (which can be determined by DSC measurements) depends on the type of polyester component used and is moreover also controllable thereby. This temperature ($T_m1$) for segments based on caprolactone units is known to be from approximately 30 to approximately 60° C., depending on the molar mass of the macromonomer.

One preferred network with a melting point as switching temperature is based on the macromonomer poly(caprolactone-co-glycolide) dimethacrylate. The macromonomer can be reacted as it stands, or can be copolymerized with n-butyl acrylate to give the AB network. The permanent shape of the stent is determined by covalent crosslinking points. The network features a crystalline phase whose melting point is capable of controlled adjustment by way of example via the comonomer ratio of caprolactone to glycolide in the range from approximately 20 to approximately 57° C. As an example n-butyl acrylate can be use to optimize the mechanical properties of the stent.

Another preferred network with a glass transition temperature as switching temperature is obtained from an ABA triblock dimethacrylate as macromonomer, characterized by a central block composed of polypropylene oxide and by end blocks A, composed of poly(rac-lactide). The amorphous networks have a very wide switching temperature range.

Examples of particularly preferred polymer networks to be used for the inventive stent are described in the following and comprise semi-crystalline shape memory polymer networks like UV crosslinked dimethacrylate networks, mixed IPN networks and urethane networks. They can be synthesized by methods known in the art. The polymer networks of the invention usually have a gel content of at least about approximately 60%, and preferably of at least about approximately 70% in the case of mixed IPN networks and even higher gel contents of at least about approximately 80% and preferably at least about approximately 90% for UV crosslinked dimethacrylate networks or urethane networks.

UV crosslinked dimethacrylate networks preferred for the present invention have a high shape recovery of at least about approximately 95%, switching temperatures from about approximately 40 to approximately 55° C. and show no significant biodegradation within about 9 month at approximately 37° C. and approximately pH 7 to 8. Preferred polymer networks of this type are poly(ε-caprolactone) dimethacrylate or urethane dimethacrylate networks that can be copolymerized with e.g. n-butylacrylate, for example poly(ε-caprolactone)-10k urethane dimethacrylate networks or poly(ε-caprolactone)-10k-dimethacrylate/n-butylacrylate networks; poly(ε-caprolactone-co-glycolide) urethane dimethacrylate networks, for example poly(ε-caprolactone-co-glycolide)-10k (97/3) urethane dimethacrylate networks; oligocarbonate-polycaprolactone block copolymer urethane dimethacrylate networks, for example oligocarbonate-polycaprolactone-10k block copolymer urethane dimethacrylate networks; poly(oligocarbonate-sebacate) urethane dimethacrylate network, for example poly(oligocarbonate-sebacate)-8k urethane dimethacrylate networks; and poly(1,6-hexamethylene-adipate)-8k urethane dimethacrylate networks, for example poly(1,6-hexamethylene-adipate)-8k urethane dimethacrylate networks. The abbreviations like "8k" or "10k" mean, that the respective prepolymer that was crosslinked had a molecular weight of approximately 8,000 g/mol or approximately 10,000 g/mol respectively and the numbers in parenthesis like (97/3) represent weight-%.

Mixed IPN networks that are preferred for the present invention have a shape recovery of at least about approximately 85%, and typically from approximately 88 to approximately 94%, have typical switching temperatures from approximately 45 to approximately 55° C. and show no significant biodegradation within about 6 month at approximately 37° C. and approximately pH 7 to 8. Such polymers are more flexible and can be processed, (e.g., extruded), more easily than the aforementioned pure UV crosslinked dimethacrylate networks and the thermoplasts that are mixed with the prepolymers before crosslinking, can be used to adjust the properties of the mixed IPN networks. Examples of mixed IPN networks that are preferred for the present invention are the aforementioned preferred UV crosslinked dimethacrylate networks polymerized in the presence of thermoplasts, in particular in the Presence of thermoplastic polyurethanes like Carbothane ® or polycaprolactones like CAPA ®. Particularly preferred mixed IPN networks of the present invention are poly(ε-caprolactone) dimethacrylate, urethane dimethacrylate or urethane tetramethacrylate networks, for example poly(ε-caprolactone)-10k urethane dimethacrylate networks or poly(ε-caprolactone)-16k urethane dimethacrylate or tetramethacrylate networks, the networks comprising from approximately 10 to approximately 80 approximately 20 to approximately 70 weight-% and particularly preferred from approximately 25 to approximately 55 weight-% thermoplastic polyurethanes like Carbothane ® or polycaprolactones like CAPA ®, wherein the thermoplastic polycaprolactones usually have a molecular weight of at least approximately 20,000 g/mol, preferably from approximately 30,000 to approximately 120,000 g/mol and particularly preferred from about approximately 40,000 g/mol to approximately 80,000 g/mol.

For urethane networks no UV crosslinking is necessary, but workpieces usually need to be processed by reaction injection molding. Such networks preferably have a shape recovery of greater than approximately 95%, switching temperatures about approximately 45 to approximately 55° C. and show no significant biodegradation within approximately 15 month at 37° C. and pH 7 to 8. Preferred materials are poly(ε-caprolactone) tetrols or blends of poly(ε-caprolactone) tetrols and diols crosslinked with aliphatic diisocyanates like trimethylhexamethylene diisocyanate (TMDI) or hexamethylene diisocyanate (HMDI), for example poly(ε-caprolactone)-16k tetrol/TMDI networks or (poly(ε-caprolactone)-16k tetrol/poly(ε-caprolactone)-10k diol)/TMDI networks.

An example useful to produce stents with two shapes in memory being interpenetrating networks (IPNs). In a preferred embodiment the covalent network is based on poly (caprolactone) dimethacrylate as macromonomer; the interpenetrating component is a multiblock copolymer composed of macrodiols based on pentadecalactone (PDL) and ε-caprolactone (PCL) and on a diisocyanate. The permanent shape of the material is determined via the covalent crosslinking points. The two transition temperatures—melting points of the crystalline phases—can be utilized as switching temperatures for a respective temporary shape. The lower switching temperature $T_{trans}1$ can be adjusted by way of the block length of the PCL in the range from approximately 30 to approximately 55° C. The upper switching temperature $T_{trans}2$ is in the range from approximately 87 to approximately 95° C.

Biodegradable materials and in particular biodegradable network materials that can be preferably used for the stent of the invention are disclosed in, for example, U.S. Pat. No. 6,160,084, WO 2004/006885 and WO 2005/028534, that are herewith incorporated in their entirety. Preferred biodegradable shape memory polymers are selected, for example from amorphous dimethacrylate or urethane dimethacrylate networks, amorphous urethane networks and amorphous multiblock copolymers.

Although readily biodegradable stents usually are not intended to be removed from the body by surgery, but should resolve instead within the body, their removal is sometimes necessary, if complications arise. It is therefore preferred to use a biodegradable stent according to the invention to be prepared for this incident.

Biodegradable amorphous dimethacrylate networks typically have a shape recovery of greater than approximately 90%, switching temperatures from approximately 20 to approximately 55° C. and can show greater than approximately 70 weight-% mass loss within about 9 month at approximately 37° C. and approximately pH 7 to 8. Preferred examples of such polymers are poly(L-lactide-co-glycolide) dimethacrylate networks or poly(L-lactide-co-glycolide) dimethacrylate/monoacrylate networls, wherein the poly(L-lactide-co-glycolide) dimethacrylate prepolymer preferably has a molecular weight of approximately 3,000 to approximately 10,000 g/mol and in particular from approximately 4,000 to approximately 7,000 g/mol and the monoacrylate is for example selected from n-butylacrylate, n- or cyclo-hexylacrylate, triethylcitrate or caprolactone 2-(methacryloyloxi) ethylester. Some of those polymers are very rigid and brittle and preferably are plasticized by known means.

Biodegradable amorphous urethane networks typically have a shape recovery of greater than approximately 90%, switching temperatures from approximately 40 to approximately 65° C. and a degradation stability of less than about 12 month at approximately 37° C. and approximately pH 7 to 8. Preferred materials of this class are based on trihydroxy terminated or tetrahydroxy terminated copolyesters based on rac-dilactide with glycolide or p-dioxanone or caprolactone and diisocyanates, wherein the diisocyanates preferably are aliphatic compounds like trimethyl hexamethylene diisocyante or hexamethylene diisocyanate.

Biodegradable amorphous multiblock copolymers typically have switching temperatures from approximately 10 to approximately 40° C. and they usually degrade to more than approximately 50 weight-% in less than one year. Preferred materials are copolymers based on oligo-caprolactone or oligo(lactide-co-glycolide) as soft segment and oligo-p-dioxanone as hard segment. Such copolymers based on oligo-caprolactone and oligo-p-dioxanone typically have shape recovery values of approximately 60 to approximately 70% and those based on oligo(lactide-co-glycolide) and oligo-p-dioxanone of about approximately 30 to approximately 60%.

It is also possible to use photosensitive networks to produce the inventive stents. Suitable photosensitive networks are amorphous and feature covalent crosslinking points, which determine the permanent shape of the stent. Another feature is a photoreactive component, or a reversibly light-switchable unit, which determines the temporary shape of the stent.

In the case of the photosensitive polymers, a suitable network is used which includes photosensitive substituents along the amorphous chain segments. On UV irradiation, these groups are capable of entering into covalent bonds with one another. If the material is deformed and irradiated with light of a suitable wavelength $\lambda 1$, the original network is additionally crosslinked. The crosslinking achieves temporary fixing of the material in the deformed condition (programming). Renewed irradiation with light of another wavelength $\lambda 2$ can in turn release the crosslinking and thus restore the original shape of the material (regeneration), because the photo-crosslinking is reversible. This type of photochemical cycle can be repeated as often as desired. The basis for the photosensitive materials is a wide-mesh polymer network which, as stated above, is transparent with respect to the radiation intended to trigger the alteration of shape, (i.e., preferably forming a UV-transparent matrix). According to the invention, preference is given to networks of the present invention based on low-molecular-weight acrylates and methacrylates which can be polymerized by a free-radical route, in particular C1-C6 (meth)acrylates and hydroxy derivatives, preference being given to hydroxyethyl acrylate, hydroxypropyl methacrytate, hydroxypropyl acrylate, poly(ethylene glycol) methacrylate and n-butyl acrylate; n-butyl acrylate and hydroxyethyl methacrylate are preferably used.

The comonomer used to produce the polymeric networks of the invention include a component which is responsible for the crosslinking of the segments. The chemical nature of this component naturally depends on the nature of the monomers.

For the preferred networks based on the acrylate monomers described above as preferred, suitable crosslinking agents are bifunctional acrylate compounds which have suitable reactivity with the starting materials for the chain segments, so that they can be reacted together. These crosslinking agents include short, bifinctional crosslinking agents, such as ethylene diacrylate, low-molecular-weight bi- or polyfunctional crosslinking agents, oligomeric, linear diacrylate crosslinking agents, such as poly(oxyethylene) diacrylates or poly(oxypropylene) diacrylates, and branched oligomers or polymers having acrylate end groups.

The inventive network include, as further component, a photoreactive component (group) which is concomitantly responsible for triggering the controllable alteration of shape. This photoreactive group is a unit which, via excitation by suitable light, preferably UV radiation, can react reversibly (with a second photoreactive group) to generate or separate covalent bonds. Preferred photoreactive groups are those capable of reversible photodimerization. Preferred photoreactive components used in the inventive photosensitive networks are various cinnamates (CA) and cinnamylacylates (GM).

It is known that cinnamic acid and its derivatives dimerize under UV light of approximately 300 nm, forming a cyclobutane. If the dimers are irradiated with UV light of smaller wavelength, approximately 240 nm, they can be cleaved again. The absorption maxima can be shifted by substituents on the phenyl ring, but always remain within the UV region. Other derivatives capable of photodimerization are 1,3-diphenyl-2-propene-1-one (chalkone), cinnamylacylic acid, 4-methylcoumarin, various ortho-substituted cinnamic acids, cinnamyloxysilanes (silyl ethers of cinnamyl alcohol).

Photodimerization of cinnamic acid and of similar derivatives is a [2+2] cycloaddition of the double bonds to give a cyclobutane derivative. The E-isomers, and also the Z-isomers, are capable of entering into this reaction. Under irradiation, E/Z-isomerization competes with the cycloaddition reaction. However, E/Z-isomerization is inhibited in the crystalline state. The various possible arrangements of the isomers with respect to one another theoretically permit 11 different stereoisomeric products (truxillic acids, truxinic acids). For the reaction, the required separation of the double bonds of two cinnamic acid groups is about 4 Å.

The networks feature a number of desirable properties. Overall, the networks are good SMP materials with high recovery values, meaning that a high percentage, usually above 90%, of the original shape is regained even on repeated passage through a cycle of changes of shape. Nor does any disadvantageous loss of mechanical properties occur here.

The SMP materials used are hydrolysable or biodegradable, because the abovementioned materials are based on aliphatic polyesters. Surprisingly, it has been found that on the one hand these materials decompose in a biocompatible manner (i.e., giving non-toxic degradation products) and at the same time the mechanical integrity of the stent is retained during the degradation process, ensuring sufficiently long functionality of the stent.

Polymers for the inventive process preferably have a transition temperature $T_{trans}$ up to approximately 60° C., preferably up to approximately 50° C., and more preferably up to approximately 45° C. The lower limit of the transition temperature preferably is above body temperature. In the context of the present invention body temperature means the temperature the stent will usually take when being implanted and in particular means the temperature the stent will maximally take when being implanted, wherein the latter case also includes pathological temperatures like fever. The body temperature therefore depends on the place where the stent is implanted and the species it is implanted in a manner known to a physician.

According to the invention, it is intended that the softening point of the polymer be below the transition temperature. The permanent shape of the stent is therefore always retained, even in the case of SMP materials.

In a preferred embodiment of the inventive process, the softening point of the polymer is below the transition temperature by from approximately 0.5 to approximately 10° C., particularly preferably by from approximately 1 to approximately 5° C., what means, that in the process of the present invention the tissue support is heated to a temperature that is below the transition temperature of the polymer used for the tissue support by from approximately 0.5 to approximately 10° C., particularly preferably by from about approximately 1 to approximately 5° C.

In another preferred embodiment of the inventive process, the softening point of the polymer is above blood temperature by at least approximately 0.5° C., preferably at least approximately 2° C. and particularly preferably at least approximately 5° C., what means, that in the process of the present invention the tissue support is heated to a temperature that is above blood temperature by at least approximately 0.5° C., preferably at least approximately 2° C. and particularly preferably at least approximately 5° C.

One particular embodiment of the inventive process is characterized in that shape memory material is used as polymer.

In another preferred embodiment of the inventive process, a shape-memory material is used as polymer for the tissue support, and, for insertion of the tissue support here, the tube shaped in its permanent shape is converted to its temporary shape via heating above the transition temperature $T_{trans}$ of the shape-memory material, and is introduced into the hollow organ, and then the permanent shape is regenerated via heating and, for removal of the tissue support with retention of the permanent shape, the tissue support is heated only to a temperature below the transition temperature $T_{trans}$, until softening occurs, and then undergoes minimally invasive withdrawal from the hollow organ.

The softening point is defined herein as the temperature, where the softening according to the invention allows to remove the stent from the body without serious harm and in particular as harmless as possible. In a preferred embodiment of the invention, the elastic modulus (E-modulus) at the softening point of the material the stent is substantially made of, is less than approximately 200 Mega Pascal (MPa), preferably less than approximately 120 MPa and particularly preferred less than approximately 80 MPa. It is also a preferred embodiment of the invention, that the E-modulus at the softening point of the material the stent is substantially made of, is at least approximately 10 MPa, preferably at least approximately 30 MPa and particularly preferred at least approximately 60 MPa below the value at blood temperature.

From the polymers described herein, preferred polymers applicable for the invention can be selected by a model experiment, wherein a stent in the form of a tube of appropriate dimensions is extruded from the polymeric material to be tested and is than deployed into a tube of glass or plastic material, in particular a silicon tube. For this experiment, for example, the silicon tube is heated by a surrounding water bath to the blood temperature defined above. If the stent can be removed at a temperature between blood and transition temperature out of the silicon tube, the polymer has passed the test.

The test preferably is also done with more complex and realistic models of body vessels to select particularly preferred stents, that pass bendings or branchings without collapsing or getting stuck.

Known methods can be used to control the temperature in the tissue support during introduction and removal from the organ. In one particular embodiment of the inventive process, the temperature in the tissue support can be controlled via a heating wire let into the polymer.

To establish the transition temperature of stents composed of SMP material, it is possible to trigger the shape-memory effect not only thermally with the aid of a heatable medium but also via use of IR radiation, NIR radiation, via application of an oscillating electrical field, and/or via UV irradiation.

The tube length of the inventive stents is generally in the range from approximately 1 to approximately 15 cm, their diameter being from approximately 1 to approximately 15 mm.

The shape of the tube of the inventive tissue supports corresponds to the shape of the tissue requiring support. Accordingly, they can have a straight or curved shape.

Minimally invasive insertion of a stent into a hollow organ can by way of example be described as follows: (1) the stent, provided on a temperature-controllable balloon catheter, undergoes minimally invasive introduction into the tubular, non-vascular organ; (2) the fitted stent is heated by means of a catheter above its $T_{trans}$ (balloon fills with warm water (liquid) or gas), or is irradiated with light of wavelength smaller than 300 nm. The stent expands and widens during this process; and (3) the stent now has its permanent shape (expanded) and the balloon catheter can be removed.

What is claimed is:

1. A process for removal of a tubular tissue support from a hollow organ of a human or of an animal,
    wherein the tubular tissue support comprises at least one shape-memory polymer having physical or covalent crosslinking points determining a permanent shape of the tissue support and at least one switching segment, the at least one switching segment having a transition temperature $T_{trans}$ at which the shape memory effect can be triggered wherein the transition temperature $T_{trans}$ of the at least one switching segment is higher than a body temperature of the human or of the animal, and the polymer further has a softening point at which the elastic modulus is less than 200 MPa, wherein the softening point is below the transition temperature $T_{trans}$,
    said process comprising the steps of heating a previously implanted and expanded tissue support to a temperature corresponding to the softening point and below the transition temperature $T_{trans}$ of the at least one switching segment until softening occurs while substantially retaining the expanded size and shape of the softened tissue support; and withdrawing the softened implanted tissue support in a minimally invasive way from the hollow organ while substantially retaining its expanded size and shape.

2. The process according to claim 1, wherein the tissue support comprises at least one of a thermoplastic, a polymer network, a blend, an interpenetrating network or a mixed interpenetrating network.

3. The process according to claim 1, wherein the tissue support comprises at least one of a urethane, a polyether, a polyester, a polycarbonate or a polyamide series.

4. The process according to claim 1, wherein the transition temperature of the polymer is up to approximately 60° C.

5. The process according to claim 1, wherein the tissue support is heated to a temperature that is below the transition temperature by approximately 0.5° C. to approximately 10° C.

6. The process according to claim 1, wherein the tissue support is heated to a temperature that is at least approximately 0.5° C. above blood temperature.

7. The process according to claim 1, wherein a diameter of the tubular tissue support is retained.

8. The process according to claim 1, wherein the tissue support is a stent.

9. The process according to claim 1, wherein the transition temperature $T_{trans}$ is higher than body temperature and up to 50° C.

10. The process according to claim 1, wherein the softening point is below the transition temperature $T_{trans}$ by 1 to 5° C.

11. The process according to claim 1, wherein at the softening point of the polymer, the elastic modulus is less than 120 MPa.

12. The process according to claim 1, wherein at the softening point of the polymer, the elastic modulus is at least 10 MPa below the value at blood temperature.

13. The process according to claim 1, wherein the shape-memory polymer is a thermoplastic elastomer comprising a multiblock copolymer.

14. The process according to claim 13, wherein the multiblock copolymer is composed of α,ω-diol polymers of poly(ε-caprolactone), poly(ethylene glycol), poly(pentadecalactone), poly(ethylene oxide), poly(propylene oxide), poly(propylene glycol), poly(tetrahydrofuran), poly(dioxanone), poly(dilactide), poly(glycolide) and poly(lactide-ran-glycolide) or of α,ω-diol copolymers of the monomers on which these polymers are based.

15. The process according to claim 1, wherein the shape memory polymer is an interpenetrating network capable of memorizing two shapes.

16. The process according to claim 15, wherein the interpenetrating network comprises a covalent network based on poly(caprolactone)dimethacrylate as macromonomer and an interpenetrating component which is a multiblock copolymer composed of macrodiols based on pentadecalactone and ε-caprolactone and on a diisocyanate.

17. A process for insertion of a tubular tissue support into a hollow organ of a human or of an animal and removal of the tubular tissue support therefrom, wherein the tubular tissue support comprises at least one shape-memory polymer having physical or covalent crosslinking points determining a permanent shape of the tissue support and at least one switching segment, the at least one switching segment having a transition temperature $T_{trans}$ at which the shape memory effect can be triggered wherein the transition temperature $T_{trans}$ of the at least one switching segment is higher than a body temperature of the human or of the animal, the polymer further has a softening point at which the elastic modulus is less than 200 MPa, wherein the softening point is below the transition temperature $T_{trans}$:

said process comprising the steps of:
inserting the tubular tissue support in its permanent shape into the hollow organ of the human or the animal, and after insertion of the tissue support,
converting the permanent shape of the tubular tissue support to its temporary expanded shape via heating above a transition temperature $T_{trans}$ of the shape-memory polymer,
heating the implanted tissue support to a temperature corresponding to the softening point and below the transition temperature $T_{trans}$ of the at least one switching segment until softening occurs while substantially retaining the expanded size and shape of the softened tissue support;
and withdrawing the softened implanted tissue support in a minimally invasive way from the hollow organ while substantially retaining its expanded size and shape.

18. The process according to claim 17, wherein control of the temperature in the tissue support takes place via a heating wire in contact with the polymer.

\* \* \* \* \*